United States Patent [19]

Brockhaus

[11] Patent Number: 4,658,452
[45] Date of Patent: Apr. 21, 1987

[54] SPORTSMAN'S PAD

[76] Inventor: Peter B. Brockhaus, Rte. 1, Owen, Wis. 54460

[21] Appl. No.: 661,906

[22] Filed: Oct. 17, 1984

[51] Int. Cl.[4] .............................................. A47G 9/06
[52] U.S. Cl. ............................................ 5/420; 5/455
[58] Field of Search ................................... 5/417–420, 5/413, 449, 455, 458, 465, 482, 483, 485, 500, 502; 428/72

[56] References Cited

U.S. PATENT DOCUMENTS

| | | | |
|---|---|---|---|
| 655,308 | 8/1900 | Robinson | 5/483 |
| 2,221,310 | 11/1940 | Gazelle | 428/658 |
| 2,442,105 | 5/1948 | Vacheron | 5/482 |
| 2,726,977 | 12/1955 | See et al. | |
| 2,736,030 | 2/1956 | Moody | |
| 2,783,834 | 3/1956 | Jaffe et al. | |
| 2,801,427 | 8/1957 | Crocker | 5/483 |
| 2,949,157 | 8/1968 | Barbito | 5/442 |
| 2,962,731 | 12/1960 | Bounds | 5/442 |
| 3,259,925 | 7/1966 | Tilles | |
| 3,268,922 | 8/1966 | Moxley | 5/420 |
| 3,577,305 | 5/1971 | Hines et al. | 428/72 |
| 3,640,831 | 2/1972 | Gardner et al. | 428/72 |
| 4,038,447 | 7/1977 | Brock | 428/178 |
| 4,326,310 | 4/1982 | Frankenburg | |

FOREIGN PATENT DOCUMENTS 1029870  5/1966  United Kingdom ............. 428/72

Primary Examiner—Gary L. Smith
Assistant Examiner—Michael F. Trettel
Attorney, Agent, or Firm—Fuller, Puerner & Hohenfeldt

[57] ABSTRACT

An insulated sportsman's pad is useful when sitting or standing on cold objects. The pad includes a flexible covering and a laminated insulator. The insulator is constructed as at least one layer of air bubbles encapsulated between heat reflecting thin flexible sheets. The bubble layers provide excellent insulation and comfort qualities. The insulator may be appropriately scored to enhance folding the sportsman's pad into a pocket sized package. The pad may include a hand warming pocket extending through the pad and between two insulators.

3 Claims, 9 Drawing Figures

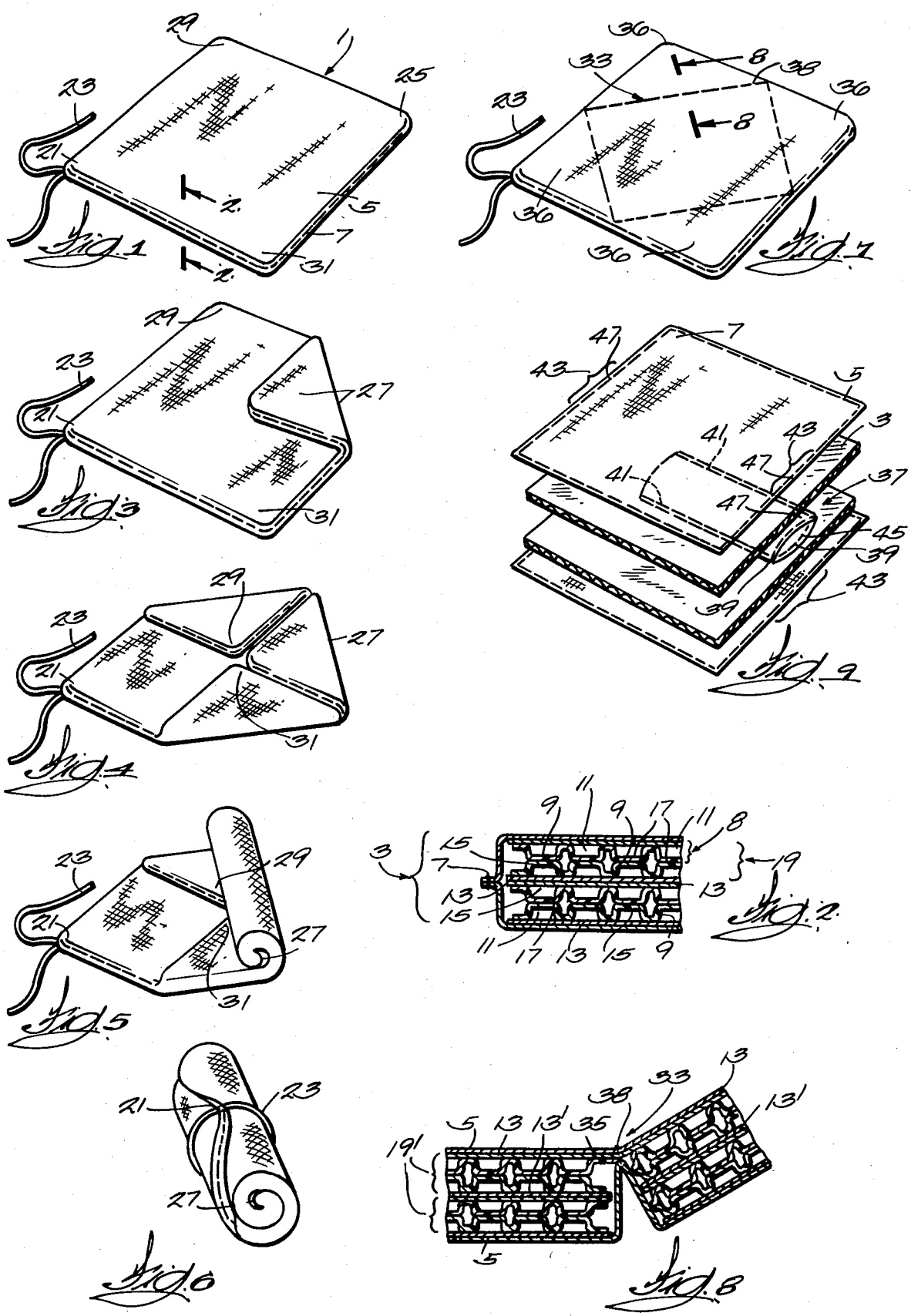

SPORTSMAN'S PAD

BACKGROUND OF THE INVENTION

1. Field of the Invention

This invention pertains to insulating apparatus, and more particularly to conveniently carryable personal insulating pads.

2. Description of the Prior Art.

Various types of insulating devices have been developed to maintain a person's comfort when he is in contact with a cold object. In particular, it is known to employ portable cushions for sitting on a tree stump or bleacher seat.

Insulating cushions in the form of polystyrene beads enclosed in a nylon covering are in common use. The polystyrene beads give a comfortable feel and have insulating qualities. However, the beads tend to bunch and shift within the covering; thus the comfort and insulating properties are reduced. The beads also tend to crush into powder with use, thereby reducing the insulating properties. A puncture of the covering permits the beads to fall out, thus destroying the value of the cushion.

U.S. Pat. No. 2,736,030 shows a hinged hunting seat worn folded inside a jacket. The seat is held in place in the jacket by suspender like elastic bands and safety pins. To use the seat the hunter pulls the front of the hinged seat from under the jacket. The seat unfolds to cover his posterior for comfortable sitting. Upon rising, the elastic bands pull the seat into the folded carrying position. The device of the U.S. Pat. No. 2,736,030 is cumbersome to attach to the jacket and is limited to sitting applications.

U.S. Pat. No. 2,738,834 discloses a folding cushion which is designed for mechanical sitting comfort only. The cushion is made of several foam rubber blocks sewn between two outer layers of fabric.

U.S. Pat. No. 3,259,925 teaches a three layered insulating cushion composed of layers of insulating polystyrene, resilient polyepeleyne, and a waterproof flexible material. The three layers are held together with adhesive tape. The layers are enclosed in a fabric casing adapted to enclose two identical cushion halves. The fabric casing is hinged so the two halves fold onto one another for portability. The purpose of the layer of resilient polyester is to make the cushion comfortable to sit on. It is expensive to employ a layer of material in addition to the insulating material merely to create comfort. Further, the materials used in the U.S. Pat. No. 3,259,925 are relatively rigid, and thus the cushion is foldable only along the casing hinges. That construction limits the portability of the cushion as it cannot be carried in a garment pocket but must usually be hand held.

Other illustrations of multi-layer insulated pads include U.S. Pat. No. 2,726,977 for a blanket used primarily in steel mills and U.S. Pat. No. 4,326,310 for an insulated mattress pad. It is apparent that the structures of the U.S. Pat. Nos. 2,726,977 and 4,326,310 render them too bulky for use as personal insulating pads.

Thus, a need exists for an easily transportable personal pad which possesses superior insulating and comfort qualities.

SUMMARY OF THE INVENTION

In accordance with the present invention, a personal insulating pad is provided which is economical, comfortable, lightweight, and easy to carry. This is accomplished by the selection and arrangement of materials to include a laminated insulator covered with a tough and durable fabric.

The laminated insulator comprises one or more layers of encapsulated air bubbles. Each layer of air bubbles may be formed by embossing a thin sheet of synthetic material such as polyetheylene with numerous closely spaced indentations. The side of the sheet containing the open sides of the indentations is bonded to the second component of the laminate, which is a flat skin of thin flexible material. Thus, air in the indentations of the first sheet is permanently captured to create a flat layer of bubbles. Preferably, the crowns of two layers of bubbles are bonded together to form an insulator of two layers of bubbles with the flat skins to the outside. More than one double layered insulator may be used in a pad. The skins may be composed of any suitable material, with the preferred material being a highly reflective foil.

The insulator is covered with a flexible fabric of waterproof or water resistant material, which may be a synthetic such as nylon. The fabric covering may be colored to suit different purposes.

In the preferred embodiment, the sportsman's pad is fabricated in a generally square shape, and a pair of tie strings are attached to one of the corners. The flexibility of the bubble insulators permits rolling the pad into a compact package, and the tie strings are utilized to hold the rolled package in place. When rolled, the pad may be inserted into a garment pocket, thereby making it convenient to carry.

To enhance the foldability of the present invention, particularly if a double-layered insulator is used, the skin of one bubble layer may be scored. The skin of the second layer then acts as a hinge which permits easy folding of the insulator and pad along the score lines. Preferably, the score lines are at 45° to the periphery of the pad because that arrangement is especially advantageous for folding. To provide additional neatness to the pad, the outer covers and the unscored skin maybe stitched together along the score lines.

The versatility of the present invention permits a pad containing two or more double layers of air bubbles to be easily folded along the score lines of the scored insulator. That is accomplished by completely severing the additional insulators along lines corresponding to the score lines of the first insulator.

Further in accordance with the present invention, the sportsman's pad may include a hand warming pocket. The pocket comprises a sleeve which extends through the interior of the pad for the full length thereof. In the preferred construction, two insulators, each composed of a double layer of air bubbles, are utilized, and the sleeve is interposed between the two insulators. The ends of the sleeve are joined, as by sewing, to opposite edges of the cover.

Other objects and advantages of the invention will become apparent to those skilled in the art from the disclosure.

BRIEF DESCRIPTION OF THE DRAWINGS

FIG. 1 is a perspective view of the sportsman's pad of the present invention;

FIG. 2 is an enlarged sectional view taken along line 2—2 of FIG. 1;

FIGS. 3, 4, 5, and 6 are perspective views showing the sequence of steps used to fold the sportsman's pad of the present invention into a pocket sized package;

FIG. 7 is a perspective view of a modification of the sportsman's pad of the present invention;

FIG. 8 is an enlarged sectional view taken along line 8—8 of FIG. 7; and

FIG. 9 is an exploded perspective view of a further modification of the present invention.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Referring to FIG. 1, an insulated pad 1 is illustrated which includes the present invention. The insulated pad finds particular usefulness for insulating a person from a cold or wet object on which he is standing or sitting. However, it will be understood that the invention is not limited to environmental applications.

FIGS. 1 and 2 show the basic construction of the present invention. A flexible insulator 3 is encased by a pair of substantially identical flexible covers 5. The covers 5 are joined along the peripheries thereof by stitchings 7. Of course, the stitchings may form a blind seam, not shown, rather than the specific seam shown in FIG. 2.

The insulator 3 is manufactured as one or more layers 8 of a moisture impervious heat reflective laminate. In the preferred embodiment, each layer 8 comprises a thin sheet 9 of flexible material, such as polyethylene, which is embossed with numerous indentations 11. The side of the sheet 9 containing the open sides of the indentations 11 is bonded to a second component of the laminated layer, which is a skin 13 of thin flexible material. The skin 13 is prefereably a reflective material such as metal foil or a metal coated synthetic material. Upon bonding the skin to the embossed sheet, air within the indentations is encapsulated into numerous small air bubbles 15. The crowns 17 of two layers maybe bonded together to create a double laminate 19 of two layers 8 of bubbles. Two or more double laminates 19 maybe encased within the covers 5, as shown in FIG. 2. The insulating laminate described is similar in construction to that described in my copending U.S. patent application Ser. No. 490,466 filed May 2, 1983.

Numerous variations of the basic laminated layer 8 are possible. For example, the bubble layer may be created by bonding the open sides of two embossed thin flexible sheets 9 to each other, and the crowns of two or more layers of that construction may be bonded together. The embossed sheet may be of a reflective material, and the skin may be clear polyetheylene.

The insulated pad 1 of the present invention has superior insulating qualities. The air trapped within the bubbles 15 prevent convection within the pad. The air bubbles also provide high resistance to heat conduction from the person to the cold object on which he is sitting or standing. The reflective skins 13 reflect heat back to the person and cold back to the object. A person can stand or sit comfortably on cold surfaces for extended times without danger of the surface drawing away his body heat.

The sportsman's pad of the present invention is exceptionally comfortable. The closed cell construction of the insulator 3 does not permit air to squeeze out during use. Consequently, the user is always supported on a cushion of air and not on the compressed solid materials of the pad.

The covers 5 may be of any suitable material. A durable and waterproof or water resistant material, such as nylon, is especially advantageous. The cover may be colored or decorated to suit any desired application. For example, the covers may be of an outdoor camouflage design to suit hunting applications.

The convenience of the sportsman's pad of the present invention is illustrated in FIGS. 3, 4, 5, and 6, which show the sequence of steps for folding the pad into a pocket sized package. One corner 21 of the pad is provided with two tie strings 23 secured to the covers 5. The corner 25 opposite the corner 21 is folded over to approximately the mid point of the pad, thereby creating fold line 27. The other two corners 29 and 31 are then folded over onto the pad, FIG. 4. The folded pad is then rolled, starting at fold line 27, toward corner 21, FIG. 5. The rolled pad is tied with strings 23 into a neat and compact package, FIG. 6, which is easily carried in a jacket pocket or other conventional holder.

To further increase the convenience of the present invention, the sportsman's pad may be constructed to facilitate folding. Referring to FIG. 7, the pad is divided along diagonal lines 33 into a generally square central panel 34 and four generally triangular corner pieces 36, and the insulator 3 is modified so that the pad readily folds along lines 33. Referring to FIG. 8, skin 13' of double laminate 19' is scored along lines 33. Skin 13 is not scored. Thus, the skin 13 forms a hinge 35 about which the laminate 19' may swing. If the sportsman's pad contains a second bubble layer 19, FIG. 8, the additional layers are completely severed along lines 33, so that the entire insulator swings about the hinges 35 of skin 13. To maintain the proper locations of the insulator pieces within the covers 5, the covers and skin 13 are sewn together by stitchings 38 along lines 33.

Further in accordance with the present invention, the sportsman's pad may include a hand warming pocket. Referring to FIG. 9, the hand warming pocket preferably takes the form of a sleeve 37 of fabric. The sleeve may be manufactured as a pair of rectangular pieces of fabric 39 sewn together near the margins thereof along stitch lines 41. The sleeve is preferably interposed between two insulators 3, each of which may consist of a double layer 19 of bubbles as described previously. The covers 5 are joined along their margins by stitchings 7, either similar to those shown in FIG. 2 or by blind seams. The stitchings 7 between the two covers are interrupted in the regions 43 so as not to close the ends of the sleeves 37. Instead, in region 43 the stitchings 45 join one sleeve piece 39 to the adjacent cover, and stitchings 47 join the second cover to the second sleeve piece. The light weight, flexibility, and insulative properties of the insulators 3 make the sportsman's pad of the present invention ideal for use as a hand warmer.

Thus, it is apparent that there has been provided, in accordance with the invention, a sportsman's pad which fully satisfies the objects, aims, and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

I claim:

1. A sportsman's pad comprising:
   a. a pair of coterminus covers of a flexible material joined together along the margins thereof; and
   b. a pair of insulators stacked one above the other between the covers, each insulator including at least one sheet of thin flexible material embossed on one side with a multiplicity of indentations, each indentation having an open side and a closed side that forms a crown, and a skin of thin flexible material bonded to the embossed sheet on the open side of the indentations to encapsulate the air therein to create a layer of encapsulated air bubbles, said thin sheet of embossed material is clear polyethylene, and the thin skin is a heat reflective material and wherein each insulator comprises two like layers of encapsulated air bubbles, and wherein the crowns of the layers are bonded together to form a double layer of bubbles,
   c. the pair of covers and the insulators are of substantially square shape;
   d. the lower double layer of encapsulated bubbles is severed along lines diagonal to the margins of the covers to create a substantially square central panel and four triangular corner pieces;
   e. the upper double layer of encapsulated bubbles is scored through one skin thereof remote from the cover along diagonal lines corresponding to the severed lines of the lower double layer of bubbles, the unscored skin of the upper double layer of bubbles thereby creating hinges for permitting swinging of the upper layer thereabout; and
   f. the covers and the unscored skin of the upper double layer of bubbles are stitched together along the diagonal lines,
   so that folding the sportman's pad along the diagonal lines is facilitated and tie means connected to an outside corner of said pad for securing said pad in a roll, said tie means having a sufficient length to encircle said rolled pad when three of said corner panels are folded and said fourth corner panel is rolled over the rolled folded corner panels to maintain said pad in said roll.

2. The sportsmans's pad of claim 1 wherein the thin sheet of embossed material is clear polyethylene, and the thin skin is a heat reflective material.

3. A sportsman's pad comprising:
   a. a pair of square coterminus covers of a flexible material joined together along the margins thereof; and
   b. an insulator interposed between the covers, the insulator including at least one sheet of thin flexible material embossed on one side with a multiplicity of indentations, each indentation having an open side and a closed side, and a skin of thin flexible material bonded to the embossed sheet on the open side of the indentations to encapsulate the air therein to create a layer of encapsulated air bubbles, two like layers being bonded together to form the insulator, and wherein one skin of the insulator is scored along lines diagonal to the margins of the covers to divide the insulator into a substantially square central panel and four triangular corner pieces, the other skin of the insulator being unscored thereby creating hinges for permitting swinging of the insulator thereabout; and the covers and the unscored insulator skin are stitched together along the diagonal lines,
   so that said corner pieces can be folded inwardly with outside pad corners centered over the pad center and one of said corner pieces having tie means, said tie means having a sufficient length to encircle a roll made from said folded other corner pieces when said unfolded corner piece is rolled over the roll formed from said folded corner pieces.

* * * * *